US007074227B2

(12) United States Patent
Portney

(10) Patent No.: US 7,074,227 B2
(45) Date of Patent: *Jul. 11, 2006

(54) IOL INSERTION TOOL WITH FORCEPS

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 561 days.

This patent is subject to a terminal disclaimer.

(21) Appl. No.: 10/318,549

(22) Filed: Dec. 12, 2002

(65) Prior Publication Data

US 2004/0116937 A1 Jun. 17, 2004

(51) Int. Cl.
*A61F 9/00* (2006.01)

(52) U.S. Cl. ..................... 606/107; 623/6.11; 623/6.12

(58) Field of Classification Search ................ 606/107, 606/166, 170, 205, 206; 623/6.11, 6.12, 623/6.18, 6.36, 6.47, 905, 906; 604/57, 59, 604/294

See application file for complete search history.

(56) References Cited

U.S. PATENT DOCUMENTS

| | | | | |
|---|---|---|---|---|
| 3,989,049 | A | | 11/1976 | Yoon |
| 4,435,855 | A | | 3/1984 | Pannu |
| 4,542,540 | A | | 9/1985 | White |
| 4,542,541 | A | | 9/1985 | Pannu |
| RE32,525 | E | | 10/1987 | Pannu |
| 4,706,666 | A | | 11/1987 | Sheets |
| 4,769,034 | A | * | 9/1988 | Poley ......................... 606/166 |
| 5,098,439 | A | * | 3/1992 | Hill et al. ................... 606/107 |
| 5,135,530 | A | | 8/1992 | Lehmer |
| 5,192,319 | A | | 3/1993 | Worst |
| 5,222,960 | A | | 6/1993 | Poley |
| 5,395,378 | A | | 3/1995 | McDonald |
| 5,562,676 | A | | 10/1996 | Brady et al. |
| 5,584,304 | A | | 12/1996 | Brady |
| 5,618,307 | A | | 4/1997 | Donlon et al. |
| 5,653,715 | A | | 8/1997 | Reich et al. |
| 5,860,986 | A | | 1/1999 | Reich et al. |
| 6,152,959 | A | | 11/2000 | Portney |
| 6,214,015 | B1 | | 4/2001 | Reich et al. |
| 6,342,058 | B1 | * | 1/2002 | Portney ...................... 606/107 |
| 6,500,181 | B1 | * | 12/2002 | Portney ...................... 606/107 |

* cited by examiner

*Primary Examiner*—Michael J. Hayes
*Assistant Examiner*—Victor Nguyen
(74) *Attorney, Agent, or Firm*—Denton L. Anderson; Sheldon & Mak PC

(57) ABSTRACT

An instrument for double-folding an elastically deformable IOL and for inserting the IOL into the anterior chamber of a patient's eye has a first elongate member and a second elongate member which are independently slidable within a handle. The distal ends of the first elongate member and the second elongate member protrude outwardly from the handle to provide a pair of forceps jaws suitable for gripping an IOL. The forceps jaws can be thrust through a double-folding member wherein the IOL is double-folded. After being double-folded, the IOL can be inserted into a patient's eye where it can be released by the forceps and allowed to unfold.

15 Claims, 5 Drawing Sheets

FIG. 11
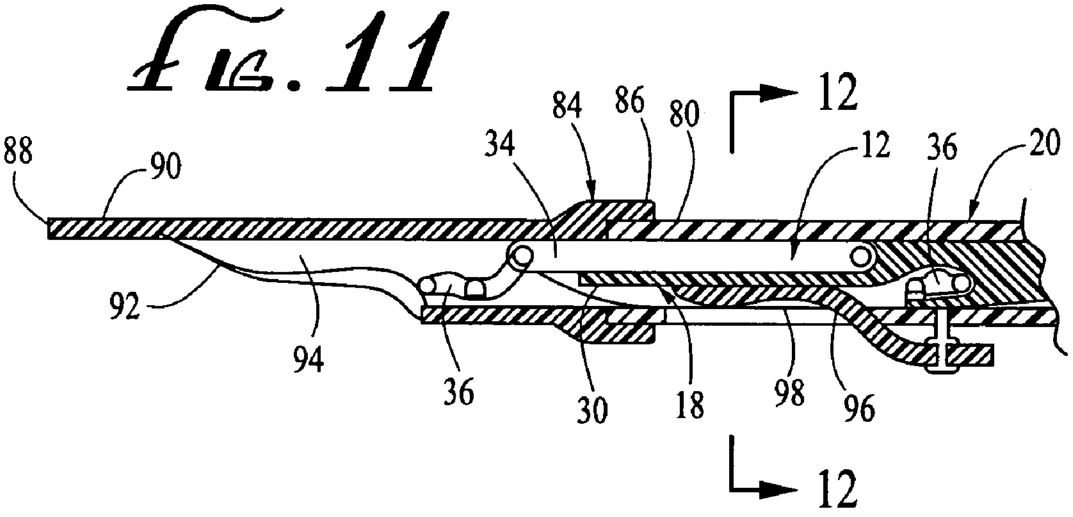
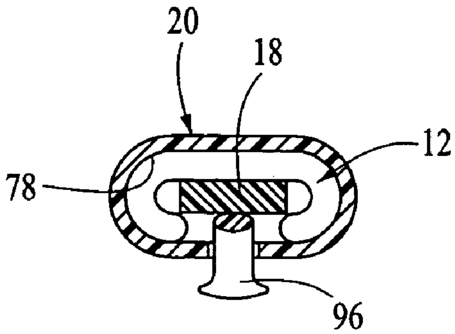
FIG. 12

IOL INSERTION TOOL WITH FORCEPS

FIELD OF THE INVENTION

This invention relates generally to insertion devices and, more specifically, to insertion devices for inserting an intraocular lens into the eye of a patient.

BACKGROUND OF THE INVENTION

Cataracts and similar degradations of the natural lens in a patient's eye are typically treated by removing the natural lens and replacing it with an artificial intraocular lens ("IOL"). Where an IOL is used to replace the patient's natural lens, the IOL is traditionally placed in the posterior portion of the eye, the portion of the eye formally occupied by the natural lens.

Recently, there has been considerable interest in developing techniques for implanting IOL's in healthy eyes to correct myopia, hyperopia, presbyopia and astigmatism. The implanting of corrective IOL's in healthy eyes can obviate the necessity of wearing spectacles and contact lenses. Where the IOL is used to correct the vision in a healthy eye, the IOL must be placed in the anterior portion of the eye, since the posterior portion of the eye remains occupied by the natural lens.

In my co-pending patent application, U.S. patent application Ser. No. 09/690,783 (the entirety of which is incorporated herein by this reference), I disclosed an insertion tool for inserting a double-folded IOL into the anterior portion of a patient's eye. That insertion tool, however, requires that the IOL be initially loaded into a holding station within the insertion tool prior to the use of the tool to insert the IOL into the eye of the patient. Having to initially load the IOL into the holding station requires that the IOL be removed from its container with a forceps and loaded into the holding station using the forceps.

It would be advantageous to be able to provide an improved insertion tool which eliminates the requirement of having to initially load the IOL into a holding station. The invention is directed to such an improved insertion tool.

SUMMARY OF THE INVENTION

The invention satisfies this need. The invention is an instrument for double-folding an elastically deformable intraocular lens ("IOL") and for inserting the double-folded IOL into the anterior chamber of a patient's eye. The instrument comprises (a) an elongate handle having a proximal end and a distal end, (b) a first elongate member slidably disposed within the handle, the first elongate member having a proximal end and a distal end, (c) a second elongate member slidably disposed within the handle, the second elongate member having a proximal end and a distal end, the distal ends of the first elongate member and the second elongate member forming an operative pair of forceps jaws for retaining an IOL, (d) means for sliding each of the elongate members back and forth within the handle and for sliding each of the distal ends of the elongate members beyond the distal end of the handle, (e) means for moving the distal end of the second elongate member with respect to the distal end of the first elongate member between (i) a closed jaw position wherein the second elongate member is disposed proximal to the first elongate member and (ii) an open jaw position wherein the second elongate member is disposed distal to the first elongate member, and (f) a double-folding member reversibly attachable to the distal end of the handle, the double-folding member comprising an open proximal end, smooth, converging interior side walls and an open distal end, the distal end being smaller than the proximal end, the converging walls being configured so as to double-fold an IOL as the IOL is moved by the forceps jaws between the proximal end of the double-folding member and the distal end of the double-folding member.

DESCRIPTION OF THE DRAWINGS

These features, aspects and advantages of the present invention will become better understood with regard to the following description, appended claims and accompanying figures where:

FIG. 11 is a cross-sectional side view of an alternative embodiment of the double-folding member and insertion tube; and FIG. 12 is a cross-sectional view of the double-folding member illustrated in FIG. 11.

DETAILED DESCRIPTION OF THE INVENTION

Figures 1, 2, 3, 4:
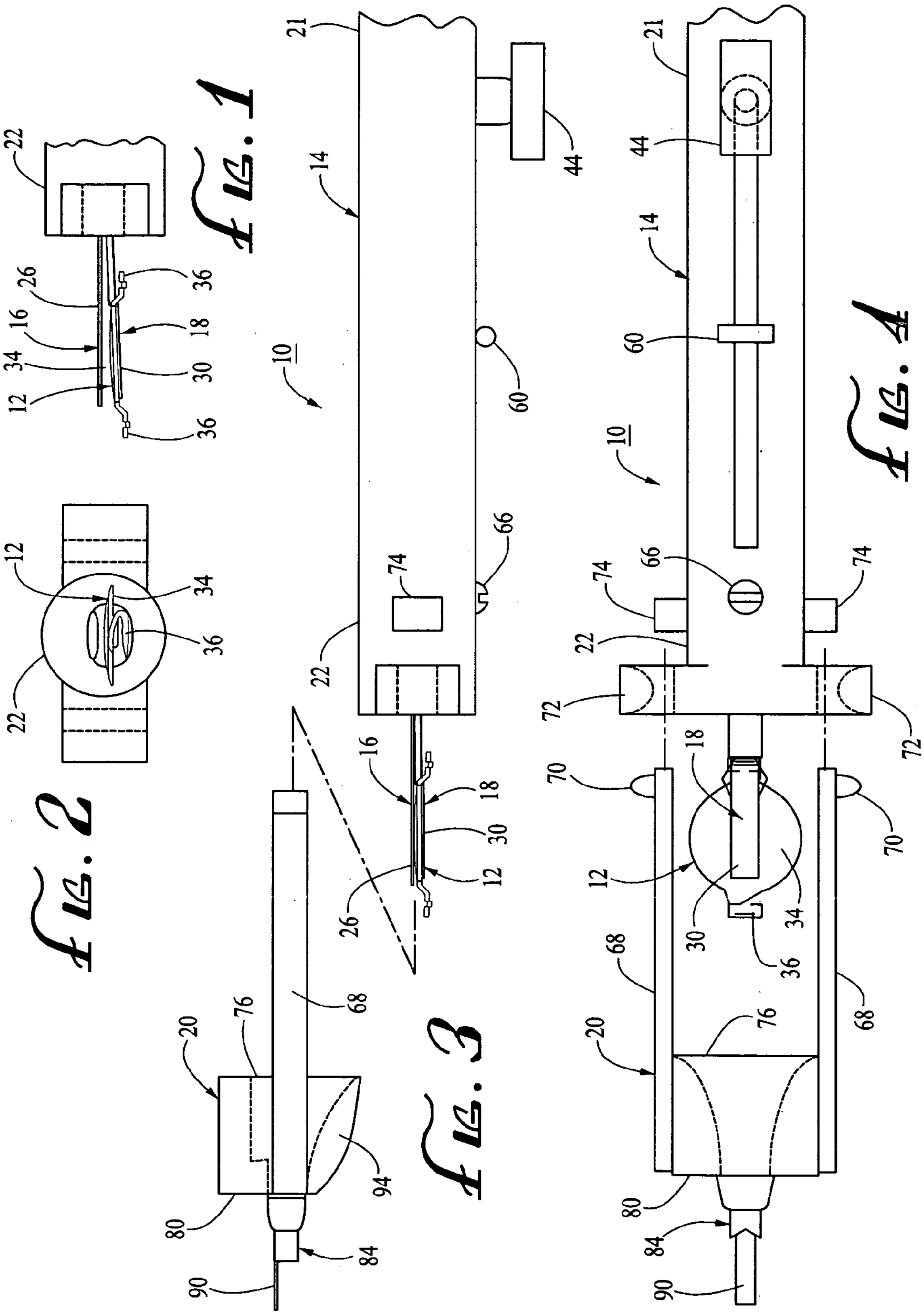
FIG. 1 is a side view of the distal end of a handle having features of the invention.
FIG. 2 is an end view of the distal end of the handle illustrated in FIG. 1.
FIG. 3 is an exploded side view of a IOL insertion tool having features of the invention.
FIG. 4 is a bottom view of the IOL insertion tube illustrated in FIG. 3.

The following discussion describes in detail one or more embodiments of the invention and several variations of that embodiment. This discussion should not be construed, however, as limiting the invention to those particular embodiments. Practitioners skilled in the art will recognize numerous other embodiments as well.

The invention is an instrument 10 for double folding an elastically deformable intraocular lens (IOL) 12 and for inserting the double folded IOL 12 into the anterior chamber of a patient's eye. The invention comprises an elongate handle 14, a pair of elongate members 16 and 18 disposed within the handle 14 and a double folding member 20.

A typical embodiment of the invention is illustrated in FIGS. 1–7E. The elongate handle 14 has an enclosed proximal end 21 and an open distal end 22. The elongate handle 14 can be made from a lightweight metal or plastic material. The handle 14 is at least about 3 inches long, and in a typical embodiment, the handle 14 is between about 4 inches long and about 5 inches long. In the embodiment illustrated in the drawings, the handle 14 has a circular cross-section but this is not necessary. Various other shapes can also be used so long as the handle 14 fits comfortably within one hand of the surgeon who will use the insertion tool. Where the handle 14 has a circular cross-section, the outside diameter of the handle 14 is typically between about 0.25 inches and about 0.5 inches.

The pair of elongate members 16 and 18 comprise a first elongate member 16 and a second elongate member 18. Both the first elongate member 16 and the second elongate member 18 are slidably disposed within the handle 14, such as by being slidably disposed within grooves defined within the handle 14. The elongate members 16 and 18 are made from a suitable rigid material, such as lightweight metals or rigid plastics. In a typical embodiment, the first elongate member 16 is between about 0.2 mm and about 2 mm in thickness and has a width of about 2.8 mm. The second elongate member 18 is 0.2 mm in thickness and is about 1.3 mm in width.

The first elongate member 16 has a proximal end 24 and a distal end 26. The second elongate member 18 has a proximal end 28 and a distal end 30. The distal ends 26 and 28 of the first elongate member 16 and the second elongate member 18 form an operative pair of forceps jaws suitable for grasping and retaining an IOL 12.

Figure 10:
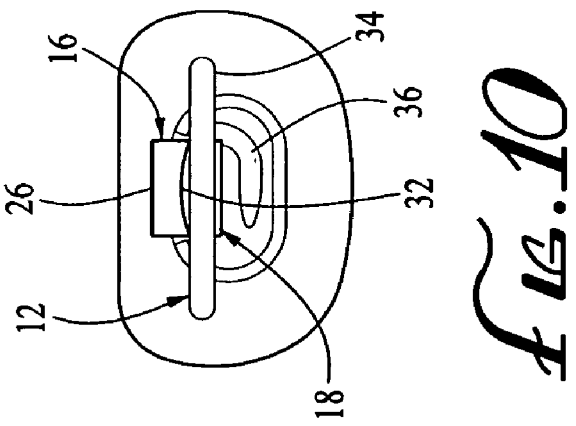
FIG. 10 is an end view of the double-folding members illustrated in FIGS. 8 and 9.

The surface 32 of the distal end 26 of the first elongate member 16 which is most proximal to the distal end 30 of the second elongate member 18 is preferably radiused to facilitate the downward bending of the IOL 12. Such an embodiment is illustrated in FIG. 10.

The first elongate member 16 and the second elongate member 18 are independently slidable within the handle 14. At the proximal end 21 of the handle 14, the first elongate member 16 and the second elongate member 18 are typically disposed proximate to one another. The distal ends 26 and 30 of the first elongate member 16 and the second elongate member 18 are disposed forward of the distal end 22 of the handle 14 where they can be used as forceps jaws. In FIGS. 1–3, the distal ends 26 and 30 of the first elongate member 16 and the second elongate member 18 are shown disposed beyond the distal end 22 of the handle 14 where they retain an IOL 12 having an optic portion 34 and a pair of opposed haptic portions 36.

Sliding means 38 are provided for sliding each of the elongate members 16 or 18 back and forth within the handle and for sliding each of the distal ends 26 and 30 of the elongate members 16 or 18 beyond the distal end 22 of the handle 14. Such sliding means 38 for sliding each of the elongate members 16 or 18 can comprise at least one slider element 40. In the embodiment illustrated in FIGS. 1–7E, the at least one slider element 40 is provided by a single slider element 42. The slider element 42 is slidably disposed in the handle 14 and has an exterior slider knob 44 disposed on the exterior of the handle 14. Within the handle 14, the slider element 44 has interior edges 46 which are disposed within slots 48 defined in each of the elongate members 16 or 18. The interior edges 46 of the slider element 42 comprise a distal edge 50 and a proximal edge 52. The proximal edge 52 is greater in length than the distal edge 52. The slider element 42 is movable in and out of the handle 14 in a direction perpendicular to the longitudinal axis 54 of the handle 14. A spring 56 or other biasing means biases the slider element 42 towards the interior of the handle 14. As is illustrated in FIGS. 7A–7E, the interior edges 46 of the slider element 42 can be moved by the slider knob 44 to contact the edges of the slots 48 defined within the elongate members 16 and 18 so as to alternatively push the elongate members 16 and 18 in the proximal or distal direction.

The sliding means 38 can be provided by many other structures commonly known to those in the art. A wide variety of other mechanical linkages and/or linkages driven by one or more tiny electrical motors can also be used.

Moving means 58 are also provided in the instrument 10 for moving the distal end 30 of the second elongate member 18 with respect to the distal end 26 of the first elongate member 16 between (i) a closed jaw position wherein the distal end 30 of the second elongate member 18 is disposed proximal to the distal end 26 of the first elongate member 16 and (ii) an open jaw position wherein the distal end 30 of the second elongate member 18 is disposed distal to the distal end 26 of the first elongate member 16. In the embodiment illustrated in FIGS. 1–7E, such moving means 58 can be provided by a biasing member 60 for biasing the second elongate member 18 towards the open jaw position and a stationary node for biasing the second elongate member 18 towards the closed jaw position when the second elongate member 18 is slid towards the distal end 22 of the handle 14. As can be seen in the embodiments illustrated in FIGS. 1–7E, the sliding of the proximal ends 24 and 28 of the first elongate member 16 and the second elongate member 18 towards the distal end 22 of the handle 14 causes the distal end 30 of the second elongate member 18 to be biased towards the first elongate member 16 as the second elongate member 18 slides past the stationary node 62. In the embodiment illustrated in the drawings, the biasing member 60 is a spring 64 and the node 62 is an adjustable lifting screw 66.

The moving means 58 can also be provided by a wide variety of other moving means commonly known in the art. A wide variety of other mechanical linkages and/or linkages driven by a tiny electric motor can also be used.

The double-folding member 20 is reversibly attachable to the distal end 22 of the handle 14. In the embodiment illustrated in the drawings, the double-folding member 20 is provided with a pair of attachment struts 68, each having opposed attachment nodes 70. The distal end of the handle 22 is provided with a pair of corresponding spring biased attachment latches 72 and a pair of opposed stops 74. Thus, in this embodiment, the double-folding member 20 is easily snapped into place on the distal end 22 of the handle 14 by thrusting the attachment struts 68 past the spring biased attachment latches 72 to the pair of stops 74. Other designs are also possible. For example, the handle 14 can be adapted to allow the distal ends 26 and 30 of the elongate members 16 and 18 to retract back into the handle 14, allowing for the double-folding member 20 to be snapped directly onto the distal end 22 of the handle 14.

The double-folding member 20 comprises an open proximal end 76, smooth converging interior side walls 78 and an open distal end 80. The distal end 80 is smaller than the proximal end 76. The converging side walls 78 are configured so as to double-fold the IOL 12 as the IOL 12 is moved by the forceps jaws between the proximal end 76 of the double-folding member 20 and the distal end 80 of the double-folding member 20. FIG. 12 illustrates an IOL 12 disposed within the double-folding member 20 and showing how the smooth converging interior side walls 78 of the double-folding member 20 act to double-fold the IOL 12, that is to fold the periphery of the optic portion 34 of the IOL 12 downwardly and then inwardly.

In the embodiment illustrated in FIGS. 1–7E, the double-folding member 20 also comprises a shoulder 82 at its distal end 80 which prevents the first elongate member 16 from exiting the distal end 80 of the double-folding member 20.

In the embodiment illustrated in FIGS. 1–7E, the double-folding member 20 further comprises an insertion tube 84 coaxially disposed at the distal end 80 of the double-folding member 20. The insertion tube 84 comprises a proximal end 86 and a distal end 88. The proximal end 86 is continuous in circumference, but the distal end 88 is discontinuous. The distal end 88 of the insertion tube 84 has an upper portion 90, an open underside 92 and a pair of opposed side wings 94. The side wings 94 are configured to allow for the gradual unfolding of the IOL 12 after the IOL 12 exits the distal end 80 of the double-folding member 20.

As illustrated in FIGS. 11 and 12, the double-folding member 20 can further comprise an optional support element 96. The support element 96 is attached to the double-folding member 20 and can be made to contact the underside of the second elongate member 18 through a slot 98 defined along the bottom of the double-folding member 20. The support element 96 provides additional support to the second elongate member 18 to prevent the second elongate member 18 from being bent or otherwise deformed during the double-folding of the IOL 12 within the double-folding member 20.

Figure 5:
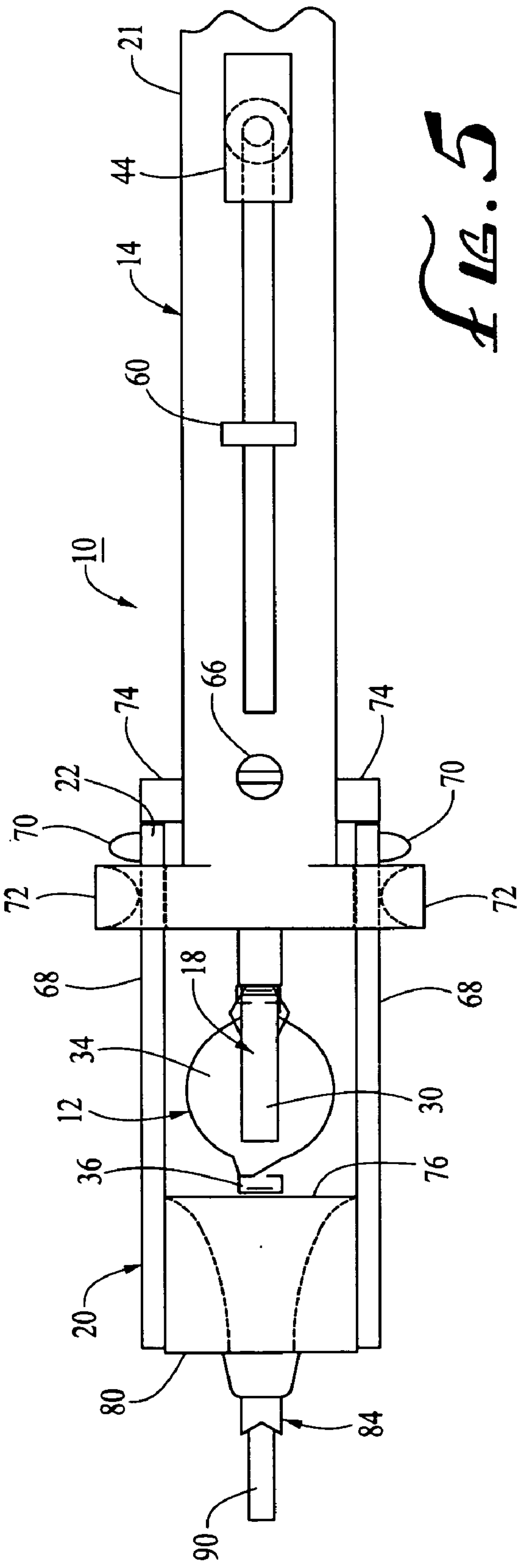
FIG. 5 is a bottom view of the IOL insertion tool illustrated in FIG. 3, shown fully assembled.
Figure 6:
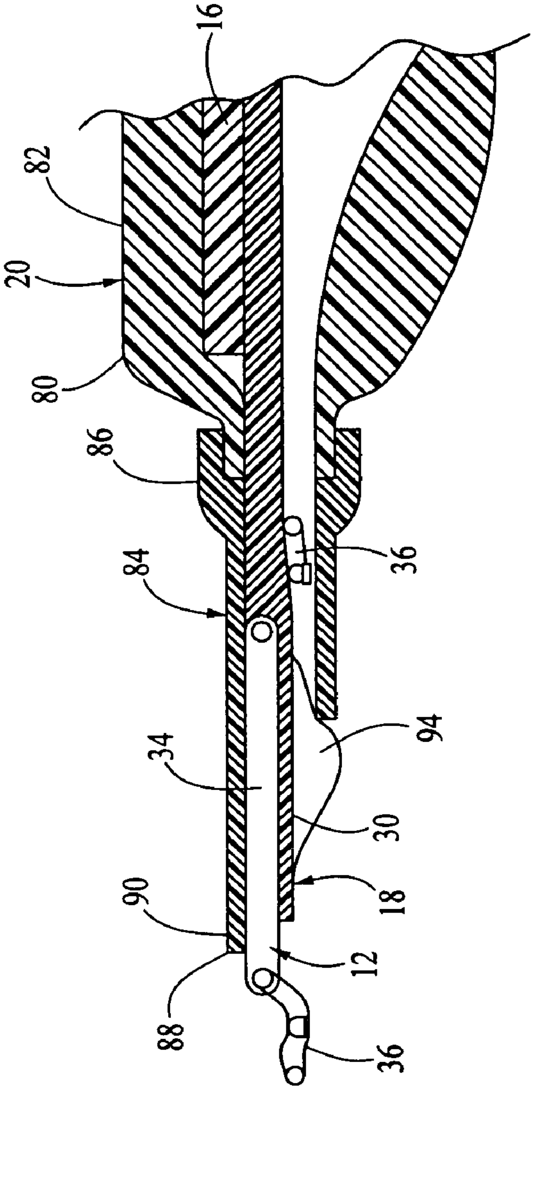
FIG. 6 is a cross-sectional side view of the an insertion tube useable in the invention.
Figure 7A:
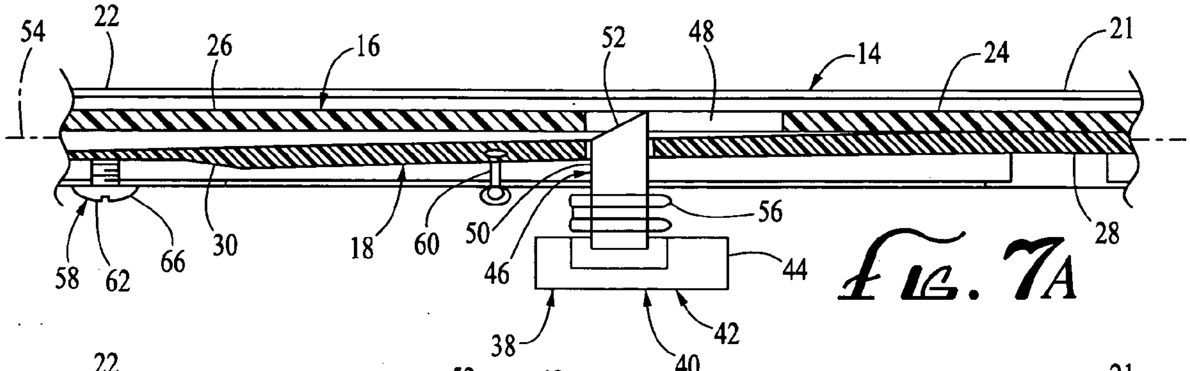
FIG. 7A is a cross-sectional side view of an elongate handle useable in the invention showing two internally disposed elongate members in a first position.
Figure 7B:
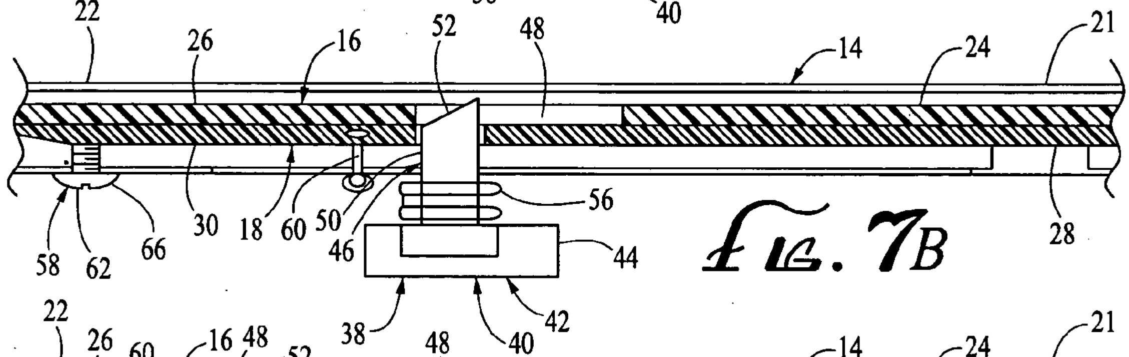
FIG. 7B is a cross-sectional side view of an elongate handle useable in the invention showing two internally disposed elongate members in a second position.
Figure 7C:
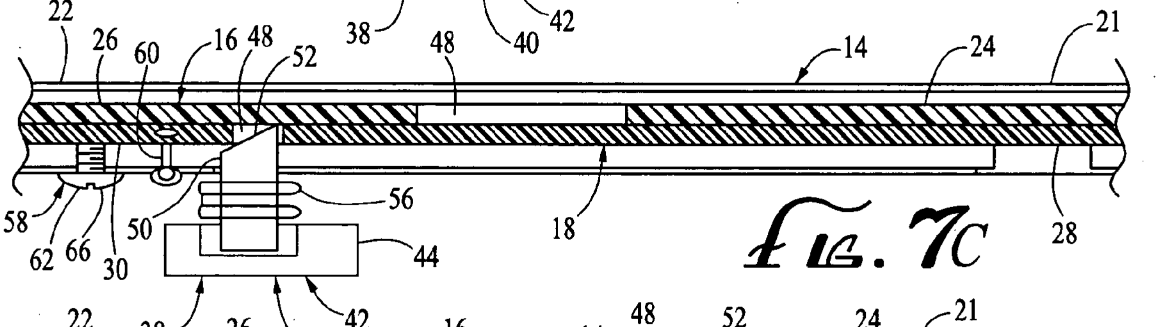
FIG. 7C is a cross-sectional side view of an elongate handle useable in the invention showing two internally disposed elongate members in a third position.
Figure 7D:
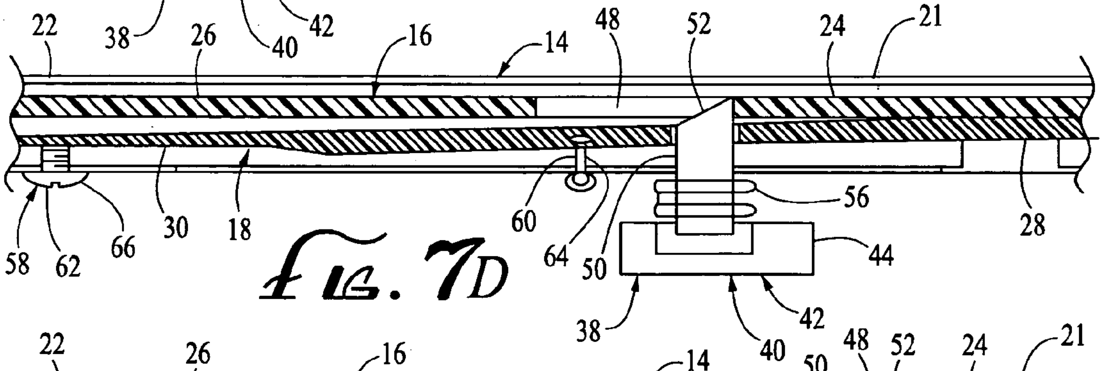
FIG. 7D is a cross-sectional side view of an elongate handle useable in the invention showing two internally disposed elongate members in a fourth position.
Figure 7E:
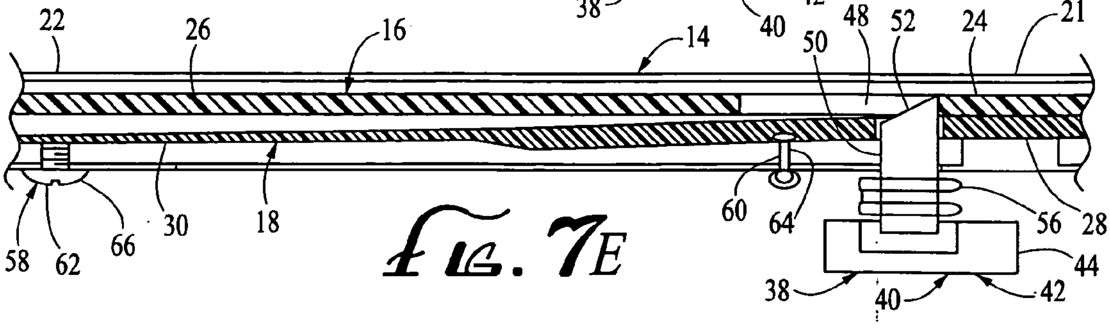
FIG. 7E is a cross-sectional side view of an elongate handle useable in the invention showing two internally disposed elongate members in a fifth position.

In operation of the embodiment illustrated in FIGS. 1–7E, the handle 14 is first disconnected from the double-folding member 20. The pair of elongate members 16 and 18 are disposed in the open jaw position by sliding the slider knob 44 towards the proximal end 21 of the handle 14. The instrument is then thrust into a container holding an IOL 12. The distal ends 26 and 30 of the elongate members 16 and 18 are positioned on opposite sides of the IOL 12, such that the IOL 12 will be axially aligned with the double-folding member 20 (illustrated in FIGS. 1 and 2). The distal ends 26 and 30 of the elongate members 16 and 18 are then moved to the closed jaw position by sliding the slider knob 44 towards the distal end 22 of the handle 14 (as illustrated in FIG. 3). The double-folding member 20 is next attached to the handle 14 by snap-connecting the attachment nodes 72 on the double-folding member 20 past the spring-biased attachment latches 72 on the handle 14. At this point, the IOL 14 and the instrument 10 are as illustrated in FIG. 5. Next, the IOL 12 is thrust through the double-folding member 20 but sliding the distal ends 26 and 30 of the elongate members 16 and 18 in the distal direction using the slider knob 44. As the IOL 12 is moved through the double-folding member 20, it is double-folded as illustrated in FIG. 12. The double-folded IOL 12 exits the distal end 80 of the double-folding member 20 and enters the proximal end 86 of the insertion tube 84. As the IOL 12 exits the distal end 80 of the double-folding member 20, the first elongate member 16 contacts the shoulder 82 on the interior of the distal end 80 of the double-folding member 20 and its movement is thereby stopped. Because the distal edge 50 of the slider element 42 is shorter than the proximal edge 52 of the slider element 42, and the slider element 42 is moveable in a direction perpendicular to the longitudinal axis 54 of the handle 14, the distal edge 50 of the slider element 42 is allowed to pass beneath the first elongate member 16 to continue pushing the second elongate member 18 after the movement of the first elongate member 16 has been stopped. The upper support of the IOL 12 is transferred to the upper portion 90 of the insertion tube 84, as illustrated in FIG. 6. The second elongate member 18 continues to push the IOL 12 through the insertion tube 84 and into the eye of a patient. As the IOL 12 approaches the distal end 88 of the insertion tube 84, the IOL 12 is allowed to gradually unfold.

Figure 8:
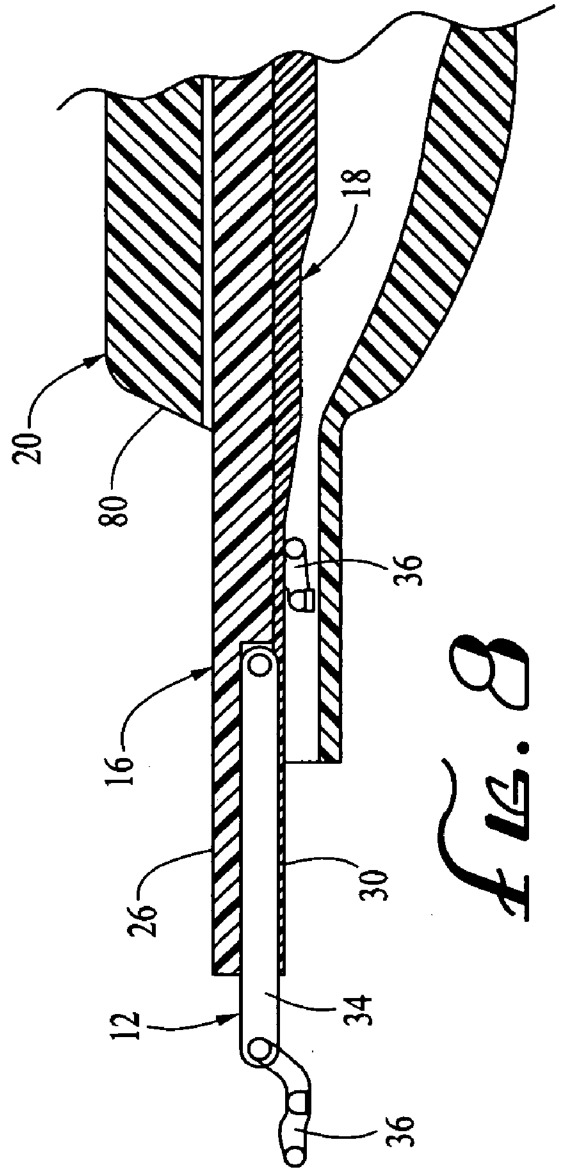
FIG. 8 is a cross-sectional side view of the distal end of a double-folding member having features of the invention, illustrating an IOL retained between a pair of forceps jaws.
Figure 9:
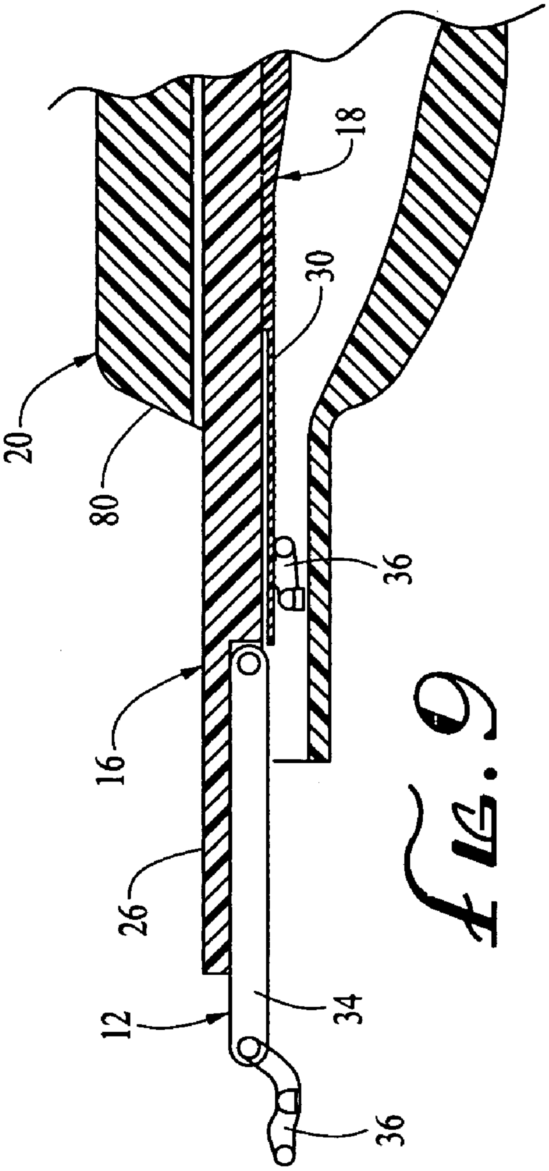
FIG. 9 is a cross-sectional side view of the distal end of a double-folding member having features of the invention, illustrating an IOL after the lower forceps jaw is retracted.

FIGS. 8–10 illustrate an alternative embodiment wherein the IOL 12 is delivered directly from the double-folding member 20 to the eye of a patient without going through an insertion tube 84. In this embodiment, the IOL 12 remains retained by both the first elongate member 16 and the second elongate member 18 as the IOL 12 is delivered to the eye of the patient. In this embodiment, the first elongate member 16 provides the pushing force for pushing the IOL 12 into the eye of the patient. The IOL 12 is allowed to gradually unfold after the distal end 30 of the second elongate member 18 is withdrawn back into the double-folding member 20. In this alternative embodiment, a longitudinal slot 100 is defined within the distal end 30 of the second elongate member 18 to retain the trailing haptic portion 36 of the IOL 12 and to allow the second elongate member 18 to withdraw into the double-folding member 20.

The invention provides a novel insertion tool for inserting a double-folded IOL into the eye of a patient. Because of the unique design of the insertion tool with extendable forceps jaws, the insertion tool of the invention eliminates the necessity of having to separately load the IOL into the insertion tool. Thus, instead of the surgeon having to remove the IOL from its packaging with a forceps and then using the forceps to position the IOL within the insertion tool, the surgeon is able to remove the IOL from its packaging with the forceps built into the insertion tool. The insertion tool therefore provides the surgeon with greater efficiency and accuracy in the insertion of a double-folded lens into the eye of a patient.

Having thus described the invention, it should be apparent that numerous structural modifications and adaptations may be resorted to without departing from the scope and fair meaning of the instant invention as set forth hereinabove and as described hereinbelow by the claims.

What is claimed is:

1. An instrument for double-folding an elastically deformable intraocular lens (IOL) and for inserting the double-folded IOL into the anterior chamber of a patient's eye, the instrument comprising:

(a) an elongate handle having a proximal end and a distal end;

(b) a first elongate member slidably disposed within the handle, the first elongate member having a proximal end and a distal end;

(c) a second elongate member slidably disposed within the handle, the second elongate member having a proximal end and a distal end, the distal ends of the first elongate member and the second elongate member being disposed forward of the distal end of the handle so as to provide an operative pair of forceps jaws for retaining an IOL;

(d) sliding means for sliding each of the elongate members back and forth within the handle;

(e) moving means for moving the distal end of the second elongate member with respect to the distal end of the first elongate member between (i) a closed jaw position wherein the distal end of the second elongate member is disposed proximal to the distal end of the first elongate member and (ii) an open jaw position wherein the distal end of the second elongate member is disposed distal to the distal end of the first elongate member; and (f) a double-folding member reversibly attachable to the distal end of the handle, the double-folding member comprising an open proximal end, smooth converging interior side walls and an open distal end, the distal end being smaller than the proximal end, the converging walls being configured so as to double-fold an IOL as the IOL is moved by the forceps jaws between the proximal end of the double-folding member and the distal end of the double-folding member.

2. The instrument of claim 1 wherein the first elongate member has an upper surface and a lower surface, the lower surface being disposed most proximal to the second elongate member, the lower surface of the first elongate member at the distal end of the first elongate member being radiused so as to facilitate the downward folding of an IOL in the double-folding member.

3. The instrument of claim 1 wherein the sliding means comprises at least one slider element, the at least one slider element being slidably disposed in the handle and having an exterior slider knob disposed on the exterior of the handle, the at least one slider element also having interior edges disposed within slots which are defined within each of the elongate members when the elongate members are in the closed open jaw position.

4. The instrument of claim 3 wherein the at least one slider element is a spring loaded single slider element and wherein the interior edges comprise a distal edge and a proximal edge, the proximal edge being of greater length than the distal edge.

5. The instrument of claim 1 wherein the moving means comprises a biasing member for biasing the second elongate member towards the open jaw position and a stationary node for biasing the second elongate member towards the closed jaw position when the proximal end of the second elongate member is slid towards the distal end of the handle by the sliding means.

6. The instrument of claim 5 wherein the biasing member is a spring and the node is an adjustable lifting screw.

7. The instrument of claim 1 wherein the double-folding member further comprises an insertion tube coaxially disposed at the distal end of the double-folding member.

8. The instrument of claim 7 wherein the double-folding member comprises a shoulder at its distal end which prevents the first elongate member from entering the insertion tube.

9. An instrument for double-folding an elastically deformable intraocular lens (IOL) and for inserting the double-folded IOL into the anterior chamber of a patient's eye, the instrument comprising:

(a) an elongate handle having a proximal end and a distal end;

(b) a first elongate member slidably disposed within the handle, the first elongate member having a proximal end and a distal end;

(c) a second elongate member slidably disposed within the handle the second elongate member having a proximal end and a distal end, the distal ends of the first elongate member and the second elongate member being disposed forward of the distal end of the handle so as to provide an operative pair of forceps jaws for retaining an IOL;

(d) sliding means for sliding each of the elongate members back and forth within the handle, the sliding means comprising at least one slider element slidably disposed in the handle and having an exterior slider knob disposed on the exterior of the handle, the at least one slider element also having interior edges disposed within slots which are defined within each of the elongate members when the elongate members are in the closed open jaw position;

(e) moving means for moving the distal end of the second elongate member with respect to the distal end of the first elongate member between (i) a closed jaw position wherein the distal end of the second elongate member is disposed proximal to the distal end of the first elongate member and (ii) an open jaw position wherein the distal end of the second elongate member is disposed distal to the distal end of the first elongate member, the moving means comprising a biasing member for biasing the second elongate member towards the open jaw position and a stationary node for biasing the second elongate member towards the closed jaw position when the proximal end of the second elongate member is slid towards the distal end of the handle by the sliding means; and (f) a double-folding member reversibly attachable to the distal end of the handle, the double-folding member comprising an open proximal end, smooth converging interior side walls and an open distal end, the distal end being smaller than the proximal end, the converging walls being configured so as to double-fold an IOL as the IOL is moved by the forceps jaws between the proximal end of the double-folding member and the distal end of the double-folding member.

10. The instrument of claim 9 wherein the double-folding member further comprises an insertion tube coaxially disposed at the distal end of the double-folding member.

11. The instrument of claim 10 wherein the double-folding member comprises a shoulder at its distal end which prevents the first elongate member from entering the insertion tube.

12. An instrument for double-folding an elastically deformable intraocular lens (IOL) and for inserting the double-folded IOL into the anterior chamber of a patient's eye, the instrument comprising:

(a) an elongate handle having a proximal end and a distal end;

(b) a first elongate member slidably disposed within the handle, the first elongate member having a proximal end and a distal end;

(c) a second elongate member slidably disposed within the handle the second elongate member having a proximal end and a distal end, the distal ends of the first elongate member and the second elongate member being disposed forward of the distal end of the handle so as to provide an operative pair of forceps jaws for retaining an IOL;

(d) sliding means for sliding each of the elongate members back and forth within the handle, the sliding means comprising a single spring loaded slider element slidably disposed in the handle and having an exterior slider knob disposed on the exterior of the handle, the slider element also having interior edges disposed within slots which are defined within each of the elongate members when the elongate members are in the closed jaw position;

(e) moving means for moving the distal end of the second elongate member with respect to the distal end of the first elongate member between (i) a closed jaw position wherein the distal end of the second elongate member is disposed proximal to the distal end of the first elongate member and (ii) an open jaw position wherein the distal end of the second elongate member is disposed distal to the distal end of the first elongate member, the moving means comprising a spring for biasing the second elongate member towards the open jaw position and an adjustable lifting screw for biasing the second elongate member towards the closed jaw position when the proximal end of the second elongate member is slid towards the distal end of the handle by the sliding means; and (f) a double-folding member reversibly attachable to the distal end of the handle, the double-folding member comprising an open proximal end, smooth converging interior side walls and an open distal end, the distal end being smaller than the proximal end, the converging walls being configured so as to double-fold an IOL as the IOL is moved by the forceps jaws between the proximal end of the double-folding member and the distal end of the double-folding member.

13. The instrument of claim 12 wherein the double-folding member further comprises a support element, the support element being disposed so as to bias the distal end of the second elongate member toward the closed jaw position when the distal end of the second elongate member is disposed at the distal end of the double-folding member.

14. The instrument of claim 12 wherein the double-folding member further comprises an insertion tube coaxially disposed at the distal end of the double-folding member.

15. The instrument of claim 14 wherein the double-folding member comprises a shoulder at its distal end which prevents the, first elongate member from entering the insertion tube.

* * * * *